United States Patent
Hishikawa

(10) Patent No.: US 9,925,095 B2
(45) Date of Patent: Mar. 27, 2018

(54) ABSORBENT ARTICLE HAVING LIQUID-PERMEABLE SECOND SHEET

(71) Applicants: LIVEDO USA, INC., Wilson, NC (US); LIVEDO CORPORATION, Osaka (JP)

(72) Inventor: Takuya Hishikawa, Wilson, NC (US)

(73) Assignees: LIVEDO USA, INC., Wilson, NC (US); LIVEDO CORPORATION, Osaka (JP)

( * ) Notice: Subject to any disclaimer, the term of this patent is extended or adjusted under 35 U.S.C. 154(b) by 106 days.

(21) Appl. No.: 14/597,582

(22) Filed: Jan. 15, 2015

(65) Prior Publication Data

US 2015/0196435 A1    Jul. 16, 2015

Related U.S. Application Data

(60) Provisional application No. 61/928,238, filed on Jan. 16, 2014.

(51) Int. Cl.
*A61F 13/15* (2006.01)
*A61F 13/539* (2006.01)
*A61F 13/511* (2006.01)
*A61F 13/49* (2006.01)
(Continued)

(52) U.S. Cl.
CPC ........ *A61F 13/539* (2013.01); *A61F 13/5116* (2013.01); *A61F 2013/49074* (2013.01); *A61F 2013/51411* (2013.01); *A61F 2013/5315* (2013.01); *A61F 2013/53925* (2013.01)

(58) Field of Classification Search
CPC ...... A61F 13/531; A61F 13/53; A61F 13/539; A61F 13/5315; A61F 13/53472; A61F 13/5349; A61F 13/53418
See application file for complete search history.

(56) References Cited

U.S. PATENT DOCUMENTS

| | | | | |
|---|---|---|---|---|
| 4,573,986 A | * | 3/1986 | Minetola | A61F 5/4401 156/276 |
| 4,826,493 A | * | 5/1989 | Martini | A61L 15/26 264/514 |

(Continued)

FOREIGN PATENT DOCUMENTS

| JP | 9-56748 A | 3/1997 |
|---|---|---|
| JP | 2001-17470 A | 1/2001 |

(Continued)

*Primary Examiner* — Bradley Philips
(74) *Attorney, Agent, or Firm* — Westerman, Hattori, Daniels & Adrian, LLP

(57) ABSTRACT

An absorbent article has an absorbing core and a liquid-permeable second sheet disposed on the absorbing core. The absorbing core includes a liquid-holding material and a liquid-permeable core-wrapping sheet. The core-wrapping sheet covers the liquid-holding material, but a portion of a top-side surface of the liquid-holding material is exposed. The second sheet contacts the liquid-holding material at the exposed portion. The second sheet is placed in direct contact with the cellulose fibers of the liquid-holding material, and liquid permeates from the second sheet into the liquid-holding material. Also, deformation of the liquid-holding material is prevented by the hydrophilic core-wrapping sheet covering the liquid-holding material.

23 Claims, 7 Drawing Sheets

(51) Int. Cl.
    *A61F 13/514*     (2006.01)
    *A61F 13/531*     (2006.01)

(56)            References Cited

U.S. PATENT DOCUMENTS

| | | | | |
|---|---|---|---|---|
| 5,649,916 | A | * | 7/1997 | DiPalma ............... A61F 13/534 604/365 |
| 5,830,202 | A | * | 11/1998 | Bogdanski ............ A61F 13/535 604/368 |
| 2002/0042600 | A1 | * | 4/2002 | Datta ................ A61F 13/49014 604/385.13 |
| 2004/0158213 | A1 | * | 8/2004 | Ponomarenko ... A61F 13/15658 604/367 |
| 2010/0249737 | A1 | * | 9/2010 | Ito .................... A61F 13/15634 604/367 |
| 2010/0312206 | A1 | * | 12/2010 | Fujioka ............. A61F 13/49466 604/365 |
| 2012/0164908 | A1 | * | 6/2012 | Kunimoto ......... A61F 13/51104 442/401 |
| 2014/0031776 | A1 | * | 1/2014 | Glaug ................... A61F 13/53 604/365 |

FOREIGN PATENT DOCUMENTS

| | | |
|---|---|---|
| JP | 2002-512082 A | 4/2002 |
| JP | 2009-148322 A | 7/2009 |

\* cited by examiner

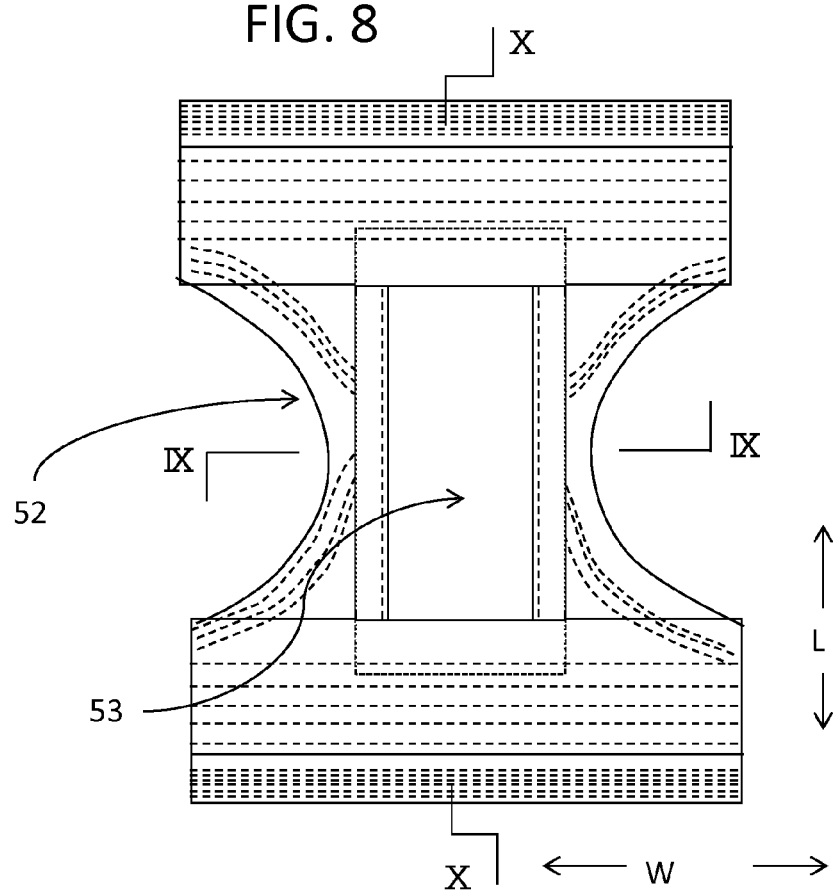
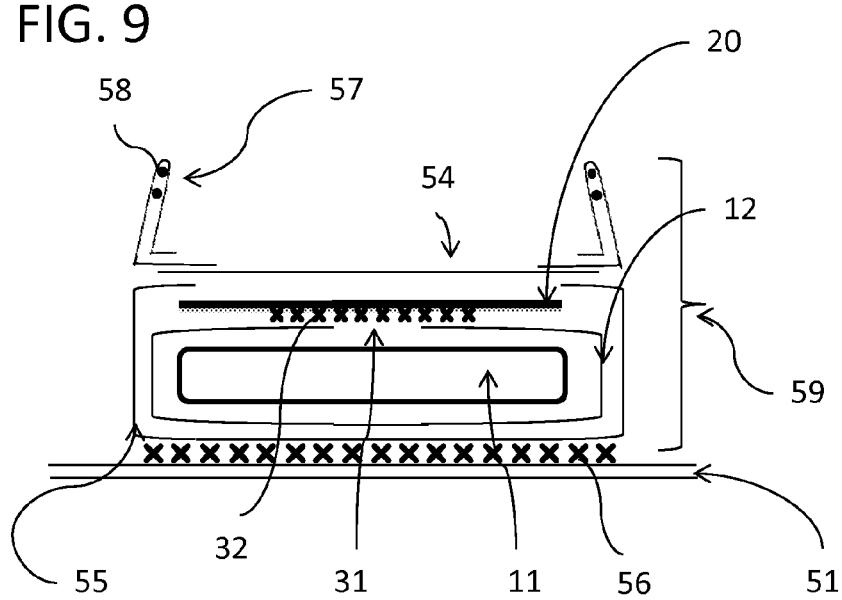

FIG.11A
FIG. 11B
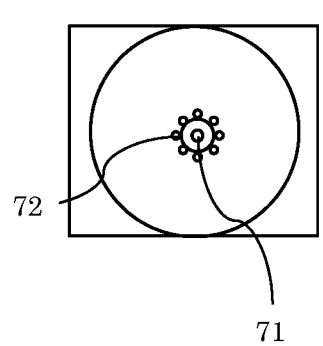
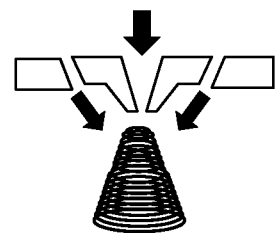
FIG. 11C
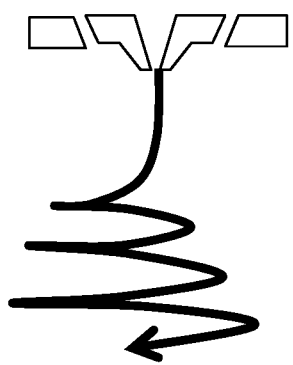

ABSORBENT ARTICLE HAVING LIQUID-PERMEABLE SECOND SHEET

CROSS-REFERENCE TO RELATED APPLICATION

This non-provisional application claims priority under 35 U.S.C. § 120 on U.S. Provisional Patent Application No. 61/928,238 filed on Jan. 16, 2014, the entire contents of which are hereby incorporated by reference.

TECHNICAL FIELD

The present invention related to an absorbent article of liquid, more particularly, absorbent articles used, for example, as urine pads, and inner pads for pull-on-type diapers and tape-on-briefs-type diapers.

BACKGROUND

Japanese Patent Application Publication No. 2001-17470 discloses an absorbing core having a tissue-like hydrophilic sheet bonded to the liquid-holding material to prevent deformation of the absorbing core. This absorbing core, however, has insufficient strength in a wet state after urination.

Japanese Patent Application Publication No. 2002-512082 discusses an absorbent article in which the entire liquid-holding material is covered with a hydrophilic non-woven cloth and is bonded to a surface sheet to prevent deformation and wetback. This technique, however, does not reduce permeation of urine from the inside to the outside of the liquid-holding material because the non-woven cloth remains hydrophilic after urination multiple times. Therefore, wetback from the liquid-holding material is not sufficiently prevented when the pressure of the body is applied thereto. Although wetback can be reduced by using an insufficiently hydrophilic non-woven cloth, it is readily conceivable that such a non-woven cloth would hinder normal absorption of urine.

Japanese Patent Application Publication No. 9-56748 discusses absorbent article in which a hydrophilic synthetic fiber layer and a sheet containing cotton pulp are disposed in layers as a second layer between a top sheet and an absorbing core to reduce wetback and urine remaining on the top sheet. Japanese Patent Application Publication No. 2009-148322 discusses an absorbent article including low-diffusion filter paper for improving the absorption rate.

Providing a second sheet is effective in improving the absorption rate and reducing wetback to a certain degree; however, the structure of the absorbing core is not disclosed in these documents. Assuming that an existing absorbing core covered in its entirety with a hydrophilic sheet such as a non-woven cloth is used, it is difficult to simultaneously reduce wetback and improve the absorption rate, as in the technique discussed in Patent Literature 2 above.

SUMMARY

The field of absorbent articles faces the challenge of improving the absorption rate and reducing wetback. Pull-on-type diapers, in particular, are often used by wearers who can walk by themselves, and they usually replace the diapers immediately after accidental urination. For such wearers, reducing leakage and discomfort due to low absorption rate is more important than increasing the absorption capacity, and there is a need for an absorbent article with a higher absorption rate. Moreover, because such wearers frequently stand up and sit down, it is necessary to eliminate the effect on skin and discomfort due to wetback from the absorbing core to the top sheet.

According to the present invention, a second sheet is disposed under a top sheet, and the second sheet can be directly bonded to a liquid-holding material in an absorbing core forming a connecting area therebetween. Upon urination, urine is directly drawn from the second sheet through the connecting area into the absorbing core. This allows the urine to be quickly directed into the liquid-holding material without being diffused. In addition, the absorber is covered with a non-woven cloth from which a hydrophilic agent readily washed away. This loss of the hydrophilic agent changes the hydrophilic non-woven cloth less hydrophilic after absorption of urine while maintaining the same strength as conventional absorbing cores, thus providing a pull-on-type absorbent article that causes little wetback.

The absorbent article of the present invention includes: the absorbing core comprising a liquid-permeable core-wrapping sheet and a liquid-holding material comprising cellulose fiber and liquid-absorbing polymer; and a liquid-permeable second sheet disposed between the top sheet and the absorbing core. The core-wrapping sheet covers the liquid-holding material at a bottom side surface, side surfaces, and a portion of a top-side surface. The liquid-holding material of the absorbing core is exposed at an exposed portion on the top-sheet-side surface, and the second sheet contacts the liquid-holding material at the exposed portion.

In the absorbent article, the exposed portion can be positioned in a central area with respect to the width direction. The core-wrapping sheet can be formed of a single piece. The liquid-permeable second sheet and the liquid-permeable core-wrapping sheet can be partially bonded. The liquid-permeable core-wrapping sheet can be formed of long-fibered non-woven cloth. The liquid-impermeable back sheet can be made of a vapor permeable material.

The liquid-holding material can have a hourglass shape where a width of the central portion with respect to the length direction L which is smaller than a width at the end portion with respect to the length direction L of the absorbing core. This shape is suitable to prevent leakage of urine at the hip and abdomen, along which urine tends to leak.

The second sheet can be disposed throughout the length of the absorbing core. The width of the second-sheet is smaller than the central width. The second sheet can be preferably formed of air-through non-woven cloth. When the second sheet is disposed throughout the length of the absorbent article, the absorption effect is improved, particularly on the side of the central portion of the absorbent article facing the hip, along which urine tend to leak. Thus, the effective absorption can be achieved at any portion of the absorbent article, which contributes to comfort.

The absorbent article has a pull-on-type can have front and back waistline areas; and a crotch area positioned between the waistline areas. Right and left leg openings are formed and the absorbing core is disposed at the crotch area.

The absorbent article can further have a liquid-permeable top sheet disposed on the liquid-permeable second sheet; and a liquid-impermeable back sheet disposed under the absorbing core.

The absorbent article can have elasticized or non-elasticized flaps on both sides with respect to the width direction of the top sheet such that liquid leakage is prevented by the stretchy flaps. The absorbent article can be an under-wear.

BRIEF EXPLANATION OF DRAWINGS

FIG. 8 is a developed view of the fourth embodiment of the present invention in FIG. 3.

FIG. 9 is a sectional view of the fourth embodiment of the present invention taken along line IX-IX in FIG. 8.

FIGS. 11A to 11C illustrate a method of distributing adhesive in a loop shape on a core-wrapping sheet or a liquid-holding material.

Figure 1:
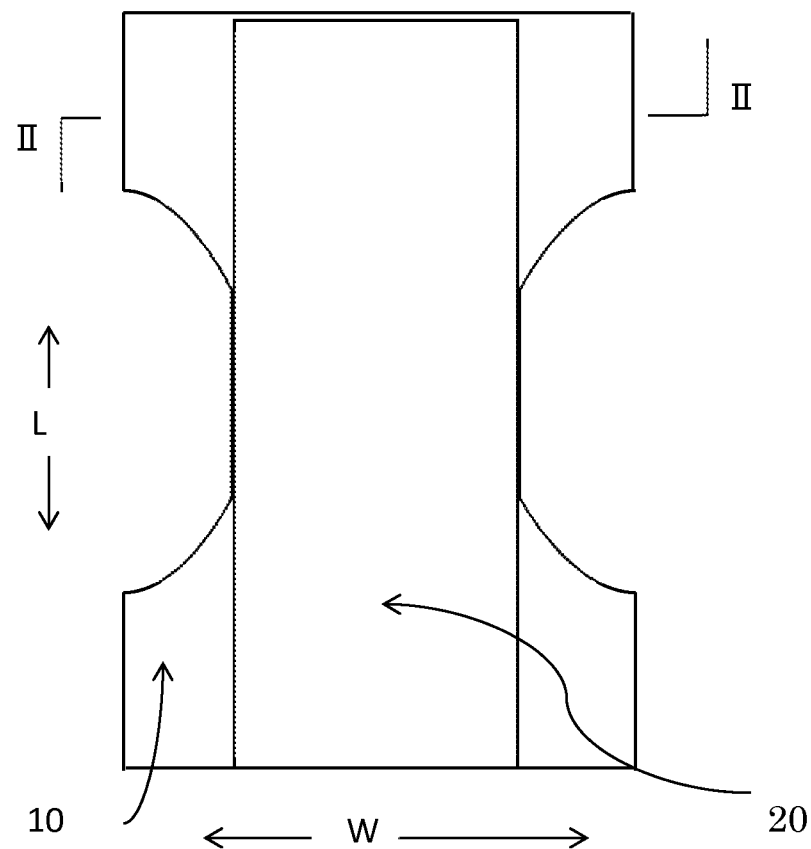
FIG. 1 is a developed view of a first embodiment of the present invention.

L: length direction
W: width direction
10: absorbing core
11: liquid-holding material
12: core-wrapping sheet
13: exposed portion
20: second sheet
31: connecting area
32: adhesive
50: pull-on-type diaper
51: exterior cover
52: leg opening
53: inner pad
54: top sheet
55: back sheet
56: adhesive
57: flap
58: flap elastic member
63: front portion
64: back portion
65: joined portion
66: belly portion
67: waistline area
68: extending portion
69: exterior cover elastic member
70: non-elastic zone
71: flap portion

DETAILED EXPLANATION

The details of embodiments of the present invention will be given with reference to FIGS. 1 to 11.

FIG. 1 is a developed view of a first example of embodiment of the present invention. FIG. 1 illustrates the arrangement of an absorbing core 10 and a second sheet 20 as viewed from the upper side. The second sheet 20 is disposed at the central portion of the absorbing core 10 in the width direction W and is extending in the length direction L throughout the length thereof. When the second sheet 20 is disposed throughout the length of the absorbent article, the absorption effect is improved, particularly on the side of the central portion of the absorbent article facing the hip, along which urine tends to leak. Thus, the effective absorption can be achieved at any portion of the absorbent article, which contributes to comfort. In addition, because the second sheet 20 covers the entire length of the exposed portion of the liquid-holding material 11, it can prevent the liquid-holding material 11 from leaking to the side facing the top sheet 54. The absorbing core 10 has an hourglass shape that is wider at both ends in the length direction L than at the central portion in the length direction L. The width of the second sheet 20 is smaller than or equal to the minimum width of the absorbing core 10, i.e., the width of the central portion in the length direction L in the figures. This shape is suitable to prevent leakage of urine at the hip and abdomen, along which urine tends to leak.

Figure 2:
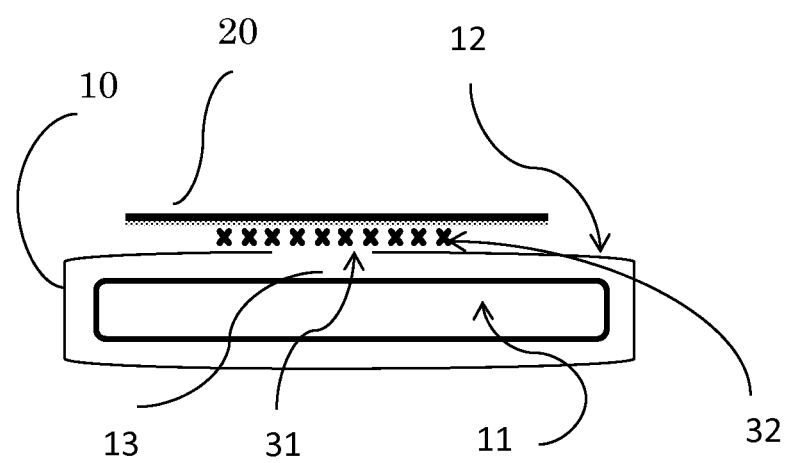
FIG. 2 is a sectional view of the first embodiment of the present invention taken along line II-II in FIG. 1.

FIG. 2 is a sectional view taken along line II-II in FIG. 1. The absorbent article includes the absorbing core 10, which includes a liquid-holding material 11 and a liquid-permeable core-wrapping sheet 12 which covers the liquid-holding material 11. The liquid-holding material 11 preferably includes cellulose fiber and liquid-absorbing polymer. A liquid-permeable second sheet 20 is disposed above the absorbing core 10. The core-wrapping sheet 12 covers the liquid-holding material 11 at a bottom side surface, side surfaces, and a portion of a top-side surface. A liquid-holding material 11 has an exposed portion 13 not covered by a core-wrapping sheet 12 on the side facing the second sheet 20 at the central portion in the width direction. This portion forms a connecting area 31 where the liquid-holding material 11 is in direct contact with the second sheet 20. The liquid-holding material 11 and the second sheet 20 can preferably be bonded at the connecting area 31 with an adhesive.

Because the absorbent article, which typically includes a single absorbing core 10, has a connecting area 31 where the second sheet 20 disposed above the absorbing core 10 is in direct contact with the liquid-holding material 11, it does not block permeation of liquid from the second sheet 20 into the liquid-holding material 11. Also, because the hydrophilic core-wrapping sheet 12 covers the liquid-holding material 11, it prevents deformation of the liquid-holding material 11.

The connecting area 31 between the second sheet 20 and the liquid-holding material 11 can be preferably positioned substantially at the central portion of the absorbing core 10 in the width direction. Such a position allows urine to flow quickly from the central portion, which receives more urine than any other portion during wearing, into the liquid-holding material 11.

The core-wrapping sheet 12 can be made of a long-fibered non-woven cloth treated with a hydrophilic agent. The hydrophilic agent can be one which can be washed away from the long-fibered non-woven cloth when urine flows through the core-wrapping sheet 12 into the liquid-holding material 11. The non-woven cloth, from which the hydrophilic agent has been washed away, becomes less hydrophilic or nearly water-repellent, the core-wrapping sheet 12 covering the liquid-holding material 11, can block wetback and retain the urine in the liquid-holding material 11 when the pressure of the body is applied thereto. Upon further urination, urine can still be absorbed into the liquid-holding material 11 because a flow of urine is formed from the second sheet 20 through the connecting area 31 into the liquid-holding material 11. The connecting area 31 can be formed with an adhesive 32 such as a hot-melt adhesive.

The core-wrapping sheet 12 and the second sheet 20 also can be bonded together. Then, even if the connecting area 31 is broken by permeation of urine, the bond between the second sheet 20 and the core-wrapping sheet 12 is structurally resistant to breakage. This reduces twisting and deformation of the liquid-holding material 11 covered by the core-wrapping sheet 12.

When the liquid-permeable core-wrapping sheet 12 is formed of a single piece, it can effectively prevent deformation of the absorbing core 10, for example, due to absorption of urine and the motion of the wearer.

The liquid-holding material 11 of the absorbing core 10 can be any material suitable for the purpose. An example of preferable material is a mixture of cellulose fibers and absorbent polymer. Adhesive such as thermoplastic adhesive also can be added to prevent the liquid-holding material 11 from losing shape. Liquid absorbent polymer absorbs and holds the liquid. Liquid absorbent polymer is typically made from acrylic acid, but other materials can be also used. Liquid absorbent polymer particles are preferably contained in the absorbing core in the range of 10 to 65 wt % of the liquid-holding material.

The core wrapping sheet can be made of a liquid permeable non-woven cloth. The examples are spun-bonded non-woven cloth made hydrophilic. Other non-woven cloths such as SMS, air through also can be used. When the core wrapping sheet is made liquid permeable and hydrophilic, it can be preferable that the hydrophilic-making agent tends to be easily washed away by the liquid so as to make the core wrapping sheet less liquid permeable in order to reduce wetback ("wetback" is a flow of liquid such as urine retained by the liquid-holding material back out of the liquid-holding material).

The second sheet 20 should be a liquid permeable sheet. The averaged basis weight is preferably 15 gms or more, more preferably 20-60 gms. The material preferably should be bulky and soft, such as air-through non-woven cloth or air-laid non-woven cloth. Also, materials other than non-woven cloth, such as a perforated film, also can be used. A soft, relatively thick air-through non-woven cloth provides improved skin comfort. Also, a thick non-woven cloth reduces wetback from the liquid-holding material when the pressure of the body is applied to the liquid-holding material.

The exterior cover 51 (outer sheet) can be made of any material which feels comfortable and which has air permeability and flexibility. Examples of preferable materials are cellulose, rayon, acetate, polyethylene, polypropylene, nylon, polyester, acrylic fiber. Liquid impermeable material is preferable. Polypropylene has advantages in strength, flexibility, and material cost. Non-woven cloth made of mixed resin of polyethylene and polypropylene, or mixed resin of polyethylene and polyethylene terephthalate can be used for the exterior cover. The non-woven cloth can be made by a process such as spun-bonding, SMS, SMMS, or point bonding. The material is preferably fusible so that the side portions can be bonded by heat.

Elastic member 69 such as elastic thread can be made of polyurethane, natural rubber, etc., which are widely used in disposable absorbent articles. Also, the elastic member 69 can be a polyurethane film ribbon.

The adhesive preferably is insoluble to the liquid to be absorbed and maintains adhesive power after getting wet. A hot-melt adhesive can be typically used and suitable one can be chosen from various kinds such as olefin series, rubber series, and rubber olefin series.

The top sheet 54 can be made of a woven or non-woven cloth of liquid permeable synthetic fabric. The synthetic fabric can be hydrophilic fabric selected from rayon, pulp, etc. The material for the top sheet 54 can be similar to that of the exterior cover. The top sheet should be liquid permeable and harmless to the human body. The examples are fabric of cellulose, rayon, acetate, polyethylene, polypropylene, nylon, polyester, acrylic. Preferable materials are spun-bonded non-woven cloth and other non-woven cloths, such as air-through, and air-laid, also can be used. It is preferable that the top sheet feels comfortable and soft and has good durability.

The back sheet 55 should be a liquid impermeable sheet to prevent the liquid from leaking on the side opposite from the human body. On the other hand, the back sheet can be either vapor permeable or impermeable. When the back sheet is vapor permeable, humidity is reduced on the side of human body.

The examples of materials for the back sheet are synthetic resin film, water shedding non-woven cloth, moisture vapor permeable film, and combination with other sheets.

The absorbent article of the present invention can be used in a pull-on-type diaper, and it will provides a comfortable thin absorbent article that is less likely to cause leakage of urine or to give a wet feeling to wearers who move actively.

Pull-on-type diapers are generally worn by people who are capable of walking, and they are also capable of putting on and taking off the diapers by themselves, and they can control their urination to some extent by themselves. The use of the absorbent article in a pull-on-type diaper provides resistance to deformation of the liquid-holding material and wetback after small-amounts multiple-time urinations when used by active users.

Figure 3:
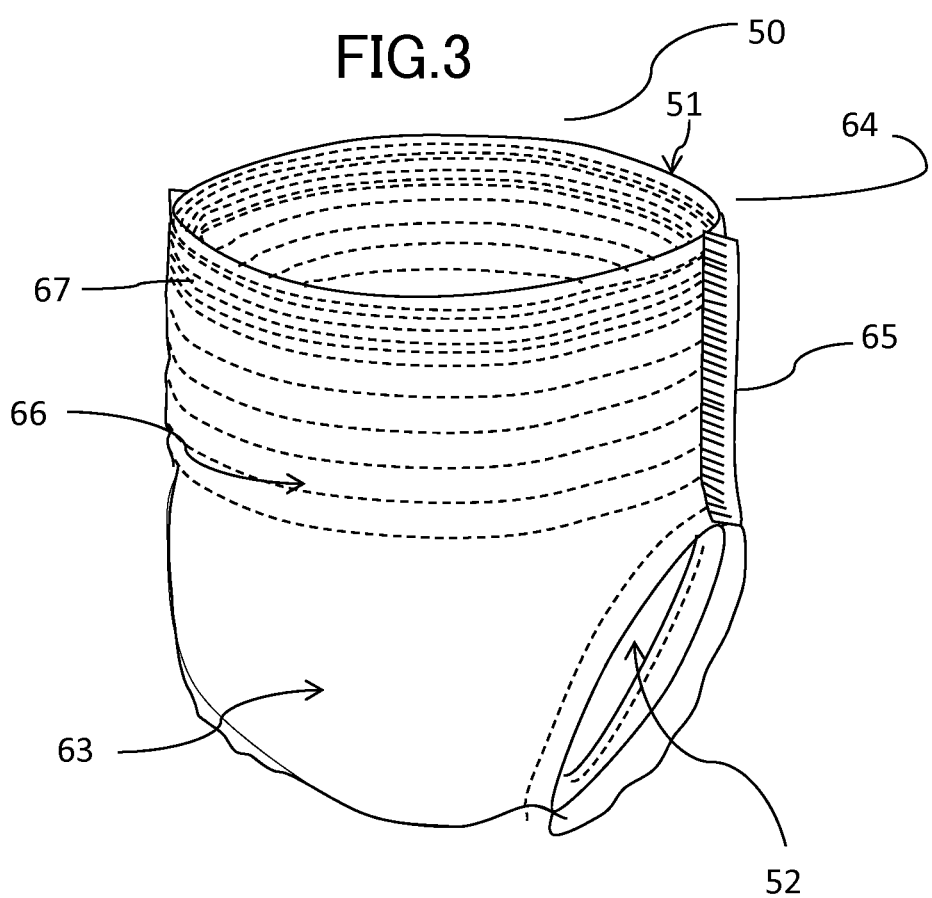
FIG. 3 is an oblique projection view of a second embodiment of the present invention applied to a pull-on-type diaper.
Figure 4:
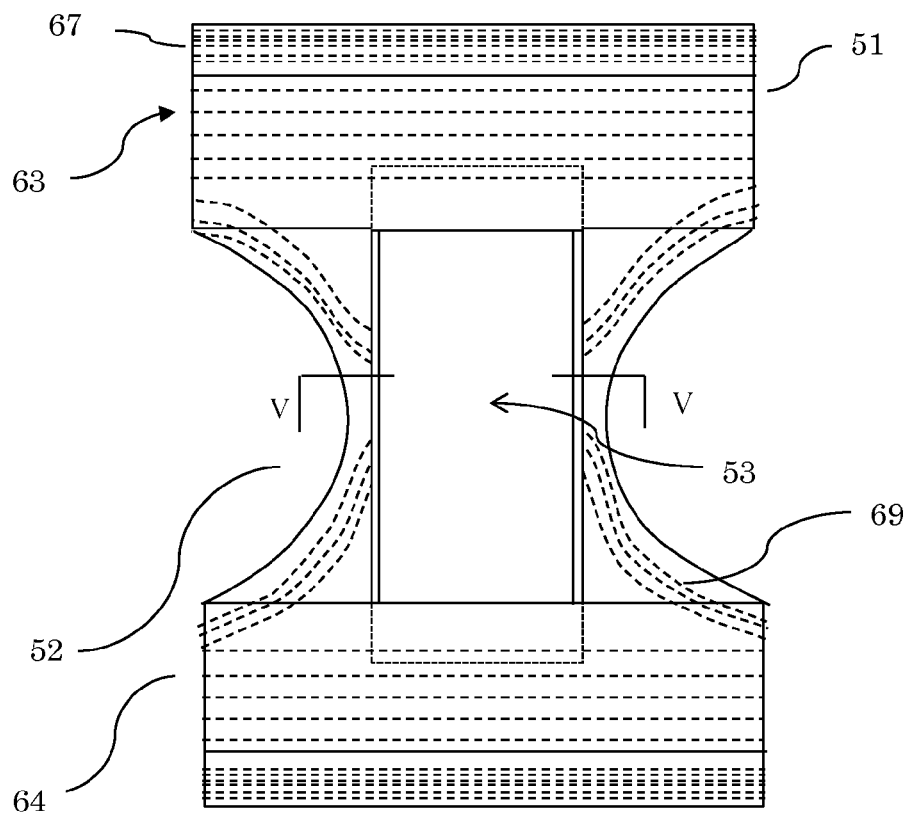
FIG. 4 is a developed view of the second embodiment of the present invention in FIG. 3.
Figure 5:
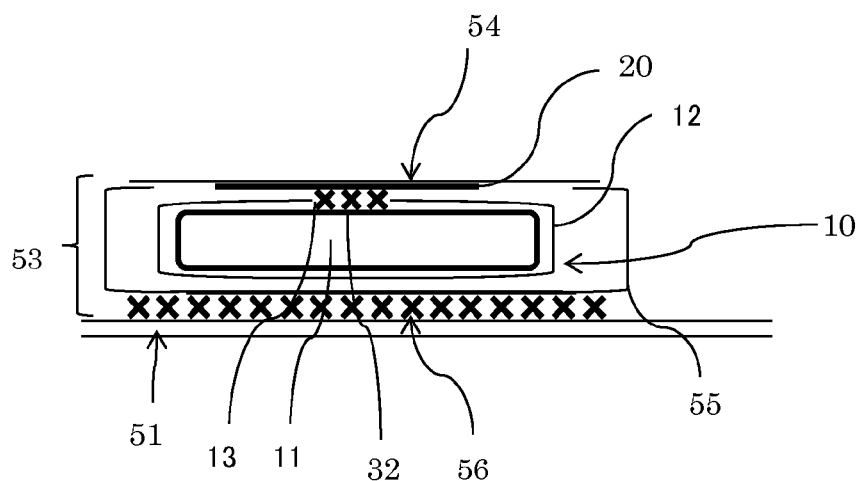
FIG. 5 is a sectional view of the second example of the present invention taken along line V-V in FIG. 4.
Figure 6:
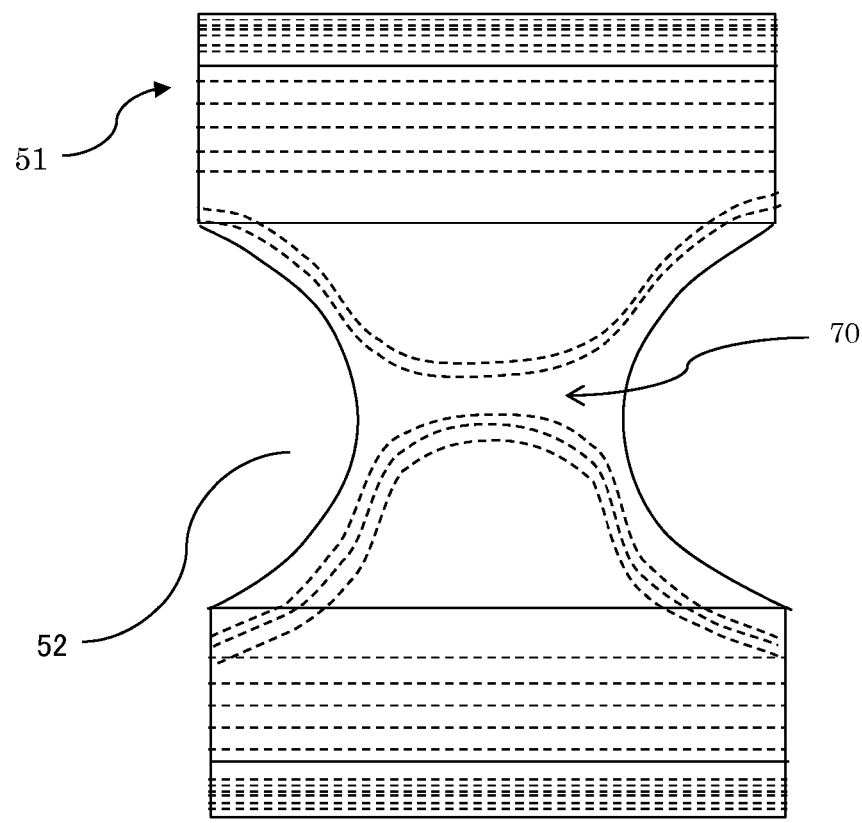
FIG. 6 is a developed view of the external cover of the pull-on-type diaper shown in FIG. 3.

FIGS. 3-6 show another example of the present invention. FIG. 3 is an overall view of the pull-on-type diaper. FIG. 4 is a developed view of the pull-on-type diaper. FIG. 5 is a sectional view taken along line V-V in FIG. 4. FIG. 6 is a developed view of the external cover of the pull-on-type diaper shown in FIG. 3.

In this embodiment, the pull-on-type diaper 50 has an elasticized waistline area 67 and a pair of leg openings 52. The front portion 63 and the back portion 64 can be joined at joined portions 65 above the upper side of the leg openings 52, and the joined portions 65 are positioned at the right and left sides of the wearer's body.

As shown in FIG. 4, an inner pad 53 is disposed between a pair of leg openings 52 inside of the exterior cover 51. The inner pad 53 can be bonded to the exterior cover 51 with an adhesive 56 such as a hot-melt adhesive.

As shown in FIG. 5, the absorbent article has a liquid-permeable second sheet 20. The inner pad 53 also is covered by a liquid-impermeable back sheet 55. The back sheet 55 of the inner pad 53 can preferably be bonded to the exterior cover 51 with an adhesive 56 such as a hot-melt adhesive.

Elastic members 69 can be attached at the leg-opening portion 52, the belly portion 66, and waistline area 67 of the exterior cover 51. The elasticity of the elastic member 69 can be changed depending on the location. The elastic member 69 makes the exterior cover 51 fit the wearer's body, and prevents leakage from around the leg or front or back portion when the wearer moves. The exterior cover 51 can have a non-elastic zone 70, for example, at the crotch area between the front portion 63 and the back portion 64 as shown in FIG. 6.

When the inner pad 53 is attached to the exterior cover 51, an adhesive 56 can be applied onto the back sheet 55 of the inner pad 53 or the exterior cover 51 by various processes such as coater process, curtain process, bead process. The inner pad 53 need not be bonded to the exterior cover 51 over the entire length as long as sufficient adhesion is obtained.

When the inner pad 53 is not bonded to the exterior cover 51 over the entire length, the end portions of the inner pad 53 can stand up causing discomfort to the wearer. Therefore, some measure may be taken to prevent it, for example, non-woven cloth or film can be overlaid on the body side at the end portions in the length direction L, as shown in FIG. 4.

The waistline area 67 preferably has elasticity such that it fits the wearer's body. For example, a ribbon elastic sheet or threads can be attached at the waistline area 67. Also, the exterior cover 51 can be made longer than the inner pad 53, and elastic members can be placed at the portion where the inner pad 53 does not overlie the exterior cover 51. The elastic portion can be folded down toward the inner pad 53.

The liquid-holding material 11 is wrapped by a core-wrapping sheet 12, such as tissue paper or non-woven cloth except the exposed area 13. The core-wrapping sheet 12 facing the liquid-holding material 11 can be bonded with the liquid-holding material 11 with an adhesive in order to prevent the absorbing core 10 from losing shape.

The liquid-holding material 11 is preferably covered with a core-wrapping sheet 12 made of a non-woven cloth made hydrophilic by a hydrophilic-making agent. The hydrophilic-making agent can be a material which tends to be easily washed away by the liquid and making the core wrapping sheet less liquid permeable or water-repellent. This can be achieved by applying a hydrophilic-making agent onto a water-repellent long-fibered non-woven cloth. Also, non-woven cloth can be manufactured from the fabric mixed with a water-soluble hydrophilic-making agent.

The core-wrapping sheet 12 facing the liquid-holding material 11 can be bonded with the liquid-holding material 11 with an adhesive in order to prevent the absorbing core 10 from losing shape.

The second sheet 20 can be bonded by an adhesive in order to prevent misalignment of the second sheet 20 and the liquid-holding material 11, and also to prevent the absorbing core 10 from losing shape. The adhesive should be applied with sufficient intervals such that the water penetration is not hindered from the second sheet 20 to the liquid-holding material 11. The adhesive preferably is of a material harmless to human body. The bonded area need not extend over the whole surface.

Figure 7:
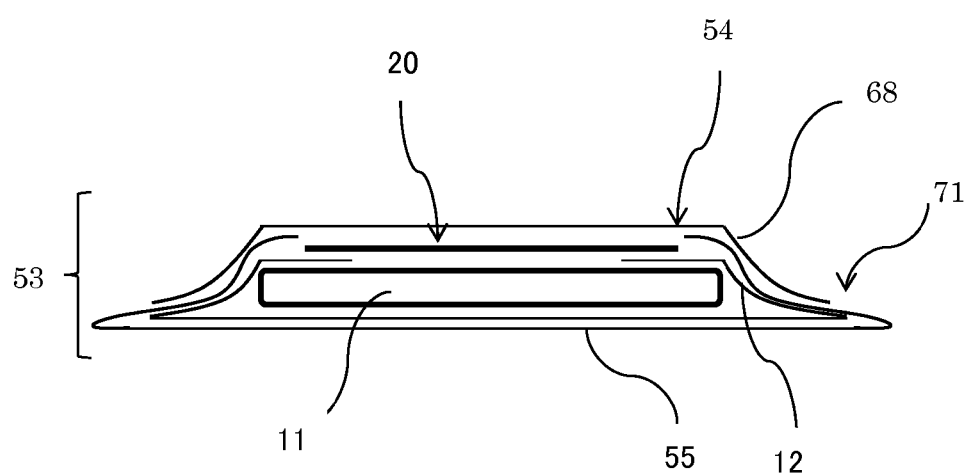
FIG. 7 is like FIG. 5, a sectional view taken along line V-V in FIG. 4 but of the third example of the present invention.

FIG. 7 shows another example of the present invention. In this example, the inner pad 53 has flap portions 71 formed by back sheet 55 and top sheet 54. The liquid-impermeable back sheet 55 is folded back at extending positions 68 extending beyond a width of the liquid-holding material 11 on both sides with respect to the width direction, and the folded-back portions form flaps. The core wrapping sheet 12 also can be folded back in a similar way.

Moreover, in this example, the liquid-permeable top sheet 54 has extending portions 68 extending beyond a width of the liquid-holding material 11. The top sheet 54 at the extending portions 68 also can form a flap portion 71 or a part of a flap portion 71.

Also, although both the liquid-impermeable back sheet 55 and the liquid-permeable top sheet 54 form the flap portions in this example, the flap portions can be formed by either one of the back sheet 55 or the top sheet 54. Even though these flap portions do not overlie the liquid-holding material 11, some urine can be temporarily held in the folded-back portions when a large amount of urine is excreted.

Figure 10:
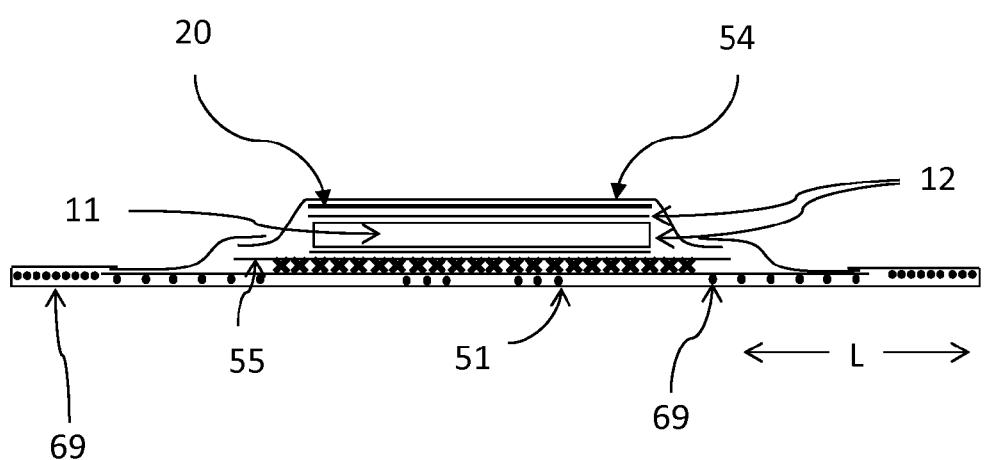
FIG. 10 is a sectional view of the fourth embodiment of the present invention taken along line X-X in FIG. 8.

FIGS. 8 and 9 illustrate another embodiment of the present invention. This is also an example of the pull-on-type diaper as shown in FIG. 3. FIG. 8 is a developed view of the pull-on-type diaper. FIG. 9 is a sectional view taken along IX-IX line in FIG. 8. FIG. 10 is a sectional view taken along line X-X in FIG. 8.

As shown in FIGS. 8 and 9, the inner pad 53 can have a top sheet 54, and flaps 57 on both sides with respect to the width direction of the top sheet 54. When a great amount of urine is discharged at a time, it takes more time until all the urine is absorbed into the absorbing core 10, and some portion can leak from the leg openings 52. The flaps 57 can prevent leakage of urine flowing toward the side surfaces. The flaps 57 can be either elasticized or non-elasticized.

The flaps 57 can be formed to stand up vertically with respect to the inner pad 53 surface when the wearer wears the diaper and the flaps 57 block the urine from flowing sideward and hold the urine inside between the flaps 57 until the liquid absorbent polymer particles absorb the urine. The flaps 57 can have an elastic member 58, preferably at the top of the flaps 57 so as to keep the flaps standing toward the wearer's body surface. The flaps can be made of a liquid impermeable sheet.

The second sheet 20 and the absorbing core 10 can be bonded by an adhesive such as hot-melt adhesive. The liquid-holding material 11 and core wrapping sheet also can be bonded by an adhesive. The two surfaces are bonded by the adhesive to prevent displacement of the two surfaces while leaving sufficient portions of the surfaces which are not covered by the adhesive such that liquid can transfer between the two surfaces. The adhesive can be preferably a hot-melt adhesive.

The adhesive can be applied on either the second sheet 20 or the core wrapping sheets by any method, such as a curtain method, a spiral method, a coating method and a bead/dot method. In the curtain method, the adhesive is sprayed such that the droplets of the adhesive are scattered on the sheet.

In a spiral method shown by FIGS. 11A to 11C, an adhesive ejecting nozzle 71 is surrounded by a number of hot-air nozzles 72. As shown by FIGS. 11B and 11C, the adhesive ejected from the adhesive-ejecting nozzle is blown by the hot air sequentially ejected from the hot-air nozzle in a rotational order such that the adhesive is spirally applied on to the sheet moving under the nozzle.

In the coating method, the adhesive is simply applied on the sheet with a thickness. Therefore, in order to partially bond the surfaces, the adhesive should be applied in a pattern. In the bead/dot method, the adhesive is applied on the sheet in a thin line or dotted line. These methods are examples of applying the adhesive, and a person of ordinary skill in the art can employ any method for the application of adhesive.

What is claimed is:
1. An absorbent article, comprising:
an absorbing core comprising a liquid-holding material and a liquid-permeable core-wrapping sheet; and
a liquid-permeable second sheet disposed on the absorbing core,
wherein the core-wrapping sheet covers the liquid-holding material at a bottom-side surface, side surfaces, and a portion of a top-side surface,
the liquid-holding material of the absorbing core is exposed at an exposed portion on the top-side surface, and
the second sheet contacts the liquid-holding material at the exposed portion,
wherein the liquid-permeable second sheet and the liquid-holding material are intermittently bonded to each other with a hot-melt adhesive, and wherein the liquid-permeable core-wrapping sheet is formed of long-fibered non-woven cloth, and a hydrophilic agent is applied to the liquid-permeable core-wrapping sheet, the hydrophilic agent being capable of being washed away by water when water flows through the core-wrapping sheet into the liquid-holding material.

2. The absorbent article according to claim 1, wherein the exposed portion is positioned in a central area with respect to the width direction.

3. The absorbent article according to claim 1, the core-wrapping sheet is formed of a single piece.

4. The absorbent article according to claim 1, wherein the liquid-permeable second sheet and the liquid-permeable core-wrapping sheet are intermittently bonded to each other with an adhesive.

5. The absorbent article according to claim 1, wherein the liquid-holding material has a hourglass shape.

6. The absorbent article according to claim 1, wherein the second sheet is disposed throughout the length of the absorbing core.

7. The absorbent article according to claim 1, wherein the width of the second-sheet is smaller than the central width of the absorbing core.

8. The absorbent article according to claim 1, wherein the second sheet is formed of air-through non-woven cloth.

9. The absorbent article according to claim 1, further comprising a liquid-permeable top sheet disposed on the liquid-permeable second sheet.

10. The absorbent article according to claim 9, wherein the liquid-permeable top sheet has extending portions extending beyond a width of the liquid-holding material, and the extending portions form flaps.

11. The absorbent article according to claim 9, wherein the absorbent article comprises no flap on either side with respect to the width direction of the liquid-permeable top sheet.

12. The absorbent article according to claim 9, further comprising flaps on both sides with respect to the width direction of the top sheet such that liquid leakage is prevented.

13. The absorbent article according to claim 12, wherein the flaps are not elasticized.

14. The absorbent article according to claim 12, wherein the flaps are elasticized.

15. The absorbent article according to claim 1, further comprising a liquid-impermeable back sheet disposed under the absorbing core.

16. The absorbent article according to claim 15, wherein the back sheet is folded back at extending positions beyond a width of the liquid-holding material on both sides with respect to the width direction, and wherein the back sheet beyond the width of the liquid-holding material forms flaps.

17. The absorbent article according to claim 16, further comprising a liquid-permeable top sheet disposed on the liquid-permeable second sheet, wherein the top sheet is extending to the extending positions, and wherein the top sheet beyond the width of the liquid-holding material also forms the flaps.

18. The absorbent article according to claim 15, wherein the back sheet is made of a vapor permeable material.

19. The absorbent article according to claim 1, wherein the liquid-holding material comprises cellulose fibers.

20. The absorbent article according to claim 1, wherein the liquid-holding material comprises liquid-absorbing polymer.

21. The absorbent article according to claim 20, wherein the liquid-absorbing polymer is mixed with cellulose fibers.

22. The absorbent article according to claim 1, wherein the liquid-holding material comprises adhesive.

23. The absorbent article according to claim 1, wherein the absorbent article is a diaper, wherein the absorbent article further comprises a pull-on-shaped exterior cover, and the absorbing core is placed inside of the diaper exterior cover.

* * * * *